United States Patent
Watanabe et al.

(10) Patent No.: US 8,551,133 B2
(45) Date of Patent: Oct. 8, 2013

(54) BALLOON CATHETER

(75) Inventors: Nobuyoshi Watanabe, Aichi (JP);
Masanori Kitagawa, Aichi (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 225 days.

(21) Appl. No.: 13/150,857

(22) Filed: Jun. 1, 2011

(65) Prior Publication Data

US 2011/0319923 A1 Dec. 29, 2011

(30) Foreign Application Priority Data

Jun. 25, 2010 (JP) ................................ 2010-145464

(51) Int. Cl.
*A61M 29/00* (2006.01)

(52) U.S. Cl.
USPC ........................................................ 606/192

(58) Field of Classification Search
USPC ........................................................ 606/194
See application file for complete search history.

(56) References Cited

U.S. PATENT DOCUMENTS

| 4,582,181 A | 4/1986 | Samson |
| 4,927,413 A | 5/1990 | Hess |
| 4,976,689 A | 12/1990 | Buchbinder et al. |
| 5,035,694 A * | 7/1991 | Kasprzyk et al. ............... 606/27 |
| 5,171,221 A | 12/1992 | Samson |
| 5,246,420 A | 9/1993 | Kraus et al. |
| 5,409,470 A | 4/1995 | McIntyre et al. |
| 5,484,409 A | 1/1996 | Atkinson et al. |
| 2002/0065475 A1 | 5/2002 | Meguro et al. |
| 2008/0161726 A1* | 7/2008 | Itou ................................ 600/585 |
| 2008/0249465 A1* | 10/2008 | Ryder et al. ............. 604/103.09 |
| 2008/0287786 A1 | 11/2008 | Lentz |
| 2009/0041923 A1* | 2/2009 | Lin et al. ......................... 427/2.3 |

FOREIGN PATENT DOCUMENTS

| EP | 0 343 509 | 11/1989 |
| JP | A-05-503872 | 6/1993 |
| JP | A-06-509244 | 10/1994 |
| JP | A-2001-204825 | 7/2001 |
| WO | WO 99/62584 | 12/1999 |

OTHER PUBLICATIONS

Aug. 19, 2011 Extended European Search Report issued in Application No. 11167578.1.
Apr. 9, 2012 Japanese Office Action issued in Japanese Patent Application No. 2010-145464 (with translation).

* cited by examiner

*Primary Examiner* — Melanie Tyson
(74) *Attorney, Agent, or Firm* — Oliff & Berridge, PLC

(57) ABSTRACT

An object of the present invention is to provide a balloon catheter integrated with a guidewire in which a stepped portion is prevented from being formed between a coil portion of the guidewire and a front end portion of the balloon catheter and thus crossability of the balloon catheter is improved. The balloon catheter includes a transition part made of resin that smoothly connects an external shape of an outer coil of a front end coil part and an external shape of a tip portion of a front side inner shaft.

5 Claims, 6 Drawing Sheets

BALLOON CATHETER

CROSS REFERENCE TO RELATED APPLICATIONS

This application is based on Japanese Patent Application No. 2010-145464 filed with the Japan Patent Office on Jun. 25, 2010, the entire content of which is hereby incorporated by reference.

TECHNICAL FIELD

The present invention relates to a balloon catheter used to dilate a stenosis or the like inside a body cavity such as a vessel.

BACKGROUND ART

Conventionally, a balloon catheter is used to dilate a stenosis or the like inside a body cavity such as a vessel. Various balloon catheters are known. In one example of balloon catheters, a guidewire for guiding a balloon catheter is accommodated in and non-removable from a body of the balloon catheter for the purpose of reducing the outer diameter or like purposes (see, for example, JP-T-6-509244, U.S. Pat. No. 5,409,470 and JP-T-5-503872).

In such a balloon catheter that is integrated with a guidewire, there has been a demand for making a difference in level between a coil portion provided at a tip portion of the guidewire and a front end portion of the balloon catheter as small as possible and for forming the coil portion and the front end portion of the catheter to be curved smoothly in an integrated manner.

Specifically, a stepped portion (in particular, a stepped portion formed by an outer diameter of an end of the catheter bigger than the outer diameter of the coil portion) may be formed between the coil portion of the guidewire and the front end portion of the balloon catheter. In this case, when the balloon catheter advances in a tortuous vessel, such a stepped portion may get stuck in an inner wall of the vessel or in a strut (a support forming meshes) of an indwelling stent or like disadvantages may be caused, which results in reduced crossability of the balloon catheter.

In the techniques disclosed in JP-T-6-509244 and U.S. Pat. No. 5,409,470, a connection structure is provided between a rear end of a coil part of a guidewire and a front end portion of a balloon catheter body. Thus, this is considered to be effective to a certain extent in reducing the difference in level between the coil part of the guidewire and the front end portion of the balloon catheter.

SUMMARY OF INVENTION

However, the connection structure disclosed in JP-T-6-509244 is to function as a valve for closing an inflation lumen of a balloon. Therefore, it is less likely that the difference in level between the coil part of the guidewire and the front end portion of the balloon catheter can be sufficiently reduced. Moreover, in the technique disclosed in this reference, liquid for dilating the balloon leaks out when the coil part of the guidewire and the front end portion of the catheter body are not in a connected state. Therefore, it is considered to be difficult to perform such an operation as turning the coil part of the guidewire around the front end portion of the catheter body.

In the connection structure disclosed in U.S. Pat. No. 5,409,470, a rear end of the coil part of the guidewire has an external shape of a screw structure. The rear end is screwed to the front end portion of the catheter body. As a result, there have been a difficulty that a smooth surface cannot be formed and a difficulty that the operating mechanism is complex owing to threads and grooves of the screw.

The present invention has been made in view of the above circumstances. An object of the present invention is to provide a balloon catheter integrated with a guidewire in which a stepped portion is prevented from being formed between a coil portion of the guidewire and a front end portion of the balloon catheter and crossability of the balloon catheter is thus improved.

The above object of the present invention is achieved by the means described below.

<1> A balloon catheter according to a first aspect of the present invention is a balloon catheter integrally accommodating a guidewire, including: a catheter body that includes a balloon, an inflation lumen for supplying a fluid for dilating the balloon and a guidewire lumen for accommodating the guidewire; a core shaft inserted in the guidewire lumen; a front end coil part formed of at least one wound strand and surrounding a front end portion of the core shaft extending from a front end of the catheter body; and a transition part made of resin that is provided at least one of a rear end of the front end coil part and a front end of the catheter body and smoothly connects an external shape of the front end coil part and an external shape of a front end portion of the catheter body.

BRIEF DESCRIPTION OF DRAWINGS

The foregoing and other objects, features, aspects and advantages of the invention will become more apparent from the following detailed description when taken in conjunction with the accompanying drawings.

DESCRIPTION OF EMBODIMENTS

Figure 1:
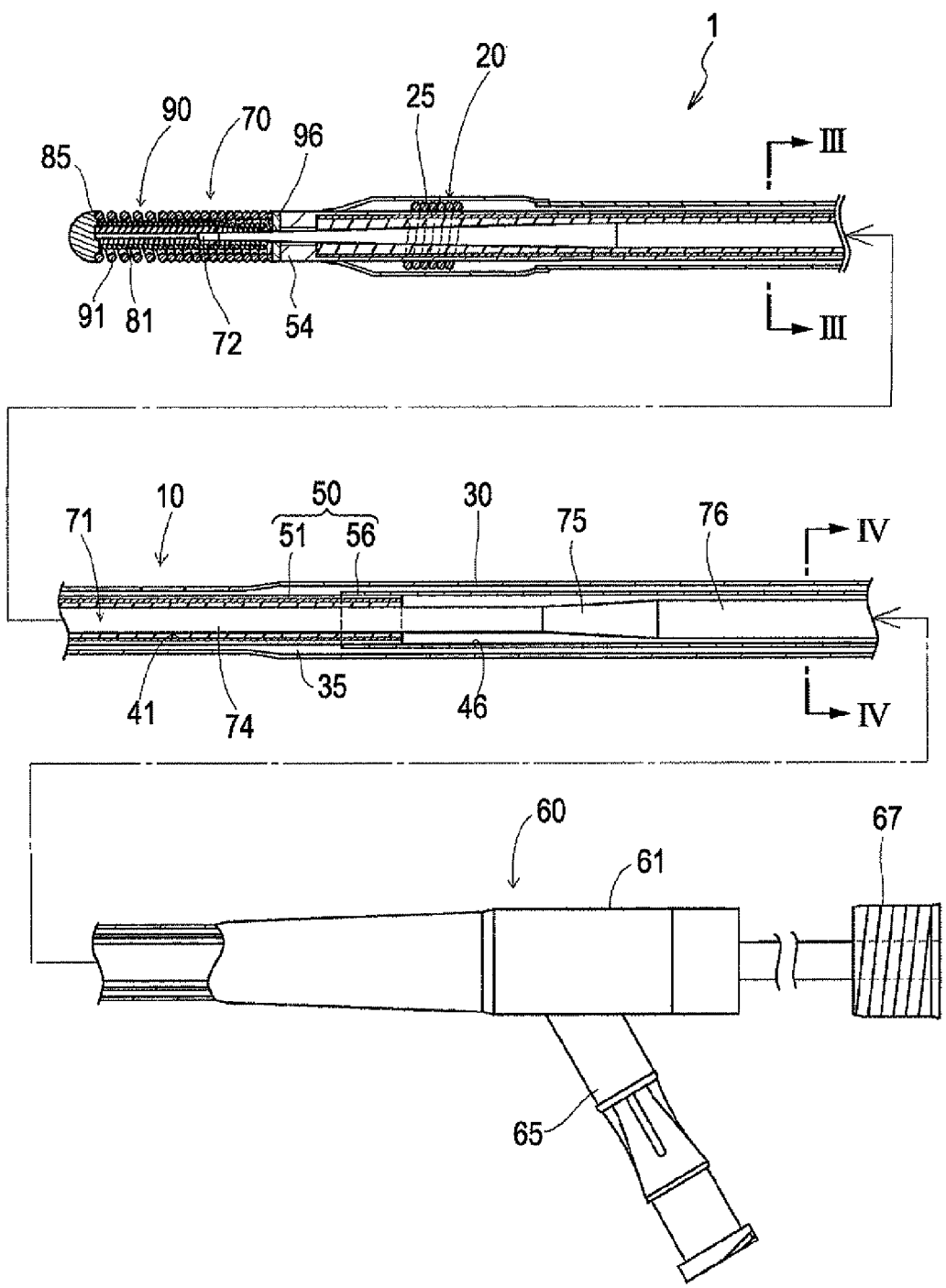
FIG. 1 is a view illustrating an entire balloon catheter according to the present embodiment.

Preferred embodiments of the present invention will be described below with reference to the accompanying drawings, in which like reference characters designate similar or identical parts throughout the several views thereof.

<1> A first aspect of the present invention is a balloon catheter integrally accommodating a guidewire, including: a catheter body that includes a balloon, an inflation lumen for supplying a fluid for dilating the balloon and a guidewire lumen for accommodating the guidewire; a core shaft inserted in the guidewire lumen; a front end coil part formed of at least one wound strand and surrounding a front end portion of the core shaft extending from a front end of the catheter body; and a transition part made of resin that is provided at least one of a rear end of the front end coil part and a front end of the catheter body and smoothly connects an external shape of the front end coil part and an external shape of a front end portion of the catheter body.

<2> A second aspect of the present invention is the balloon catheter according to the first aspect, wherein the catheter body includes a tubular outer shaft and an inner shaft that is inserted in the outer shaft and forms the guidewire lumen, the inner shaft extends from a front end of the outer shaft, and the transition part smoothly connects the external shape of the front end coil part and the external shape of the tip portion of the inner shaft.

<3> A third aspect of the present invention is the balloon catheter according to the second aspect, wherein the inner shaft includes a coil formed by winding at least one strand and a resin layer made of resin that coats the coil, and the transition part is formed integrally with the resin layer.

<1> In the balloon catheter according to the first aspect of the present invention, the external shape of the front end coil and the external shape of the catheter body are smoothly connected with the transition part therebetween. Accordingly, a stepped portion is substantially not formed between the rear end portion of the front end coil part of the guidewire and the front end portion of the catheter body. As a result, the entire balloon catheter can have a structure that is curved flexibly and smoothly. Therefore, it is possible to prevent, as much as possible, a boundary portion between the front end coil part and the catheter body from getting stuck in an inner wall of a tortuous vessel, a strut of an indwelling stent or the like, and to prevent, as much as possible, reduction in crossability of the balloon catheter caused thereby or for like reasons.

<2> In the second aspect of the present invention, the catheter body is constituted by the outer shaft and the inner shaft that is inserted in the outer shaft. In addition, the transition part is provided at the front end of the inner shaft. As a result, the transition part that connects the external shape of the front end coil and the external shape of the catheter body has a thin, substantially cylindrical shape.

Moreover, in this aspect, it is not necessary to add an extra member to the front end coil part of the guidewire. Therefore, the guidewire can fully exhibit its original characteristics. Furthermore, it is possible to prevent, as much as possible, delicate operations of the guidewire from being blocked.

<3> In the third aspect of the present invention, the inner shaft according to the second aspect includes the coil formed of at least one strand and a resin layer made of resin that coats the coil. In addition, the transition part is formed integrally with the resin layer. It is therefore possible to maintain the flexibility and also increase the stiffness of the balloon catheter. Thus, it is possible to increase the pressure resistance of the balloon catheter. Moreover, it is possible to maintain the flexibility of the inner shaft and also increase the pushing force that is a force pressing the balloon catheter in the axial direction. Furthermore, in this aspect, the resin forming the transition part is formed integrally with the resin layer that covers the coil of the inner shaft. As a result, it is possible to prevent, as much as possible, the transition part from falling off when the transition part is curved flexibly. As a result, the balloon catheter has a highly safe configuration.

The balloon catheter according to the present embodiment will be described with reference to FIGS. 1 to 5.

Figure 2:
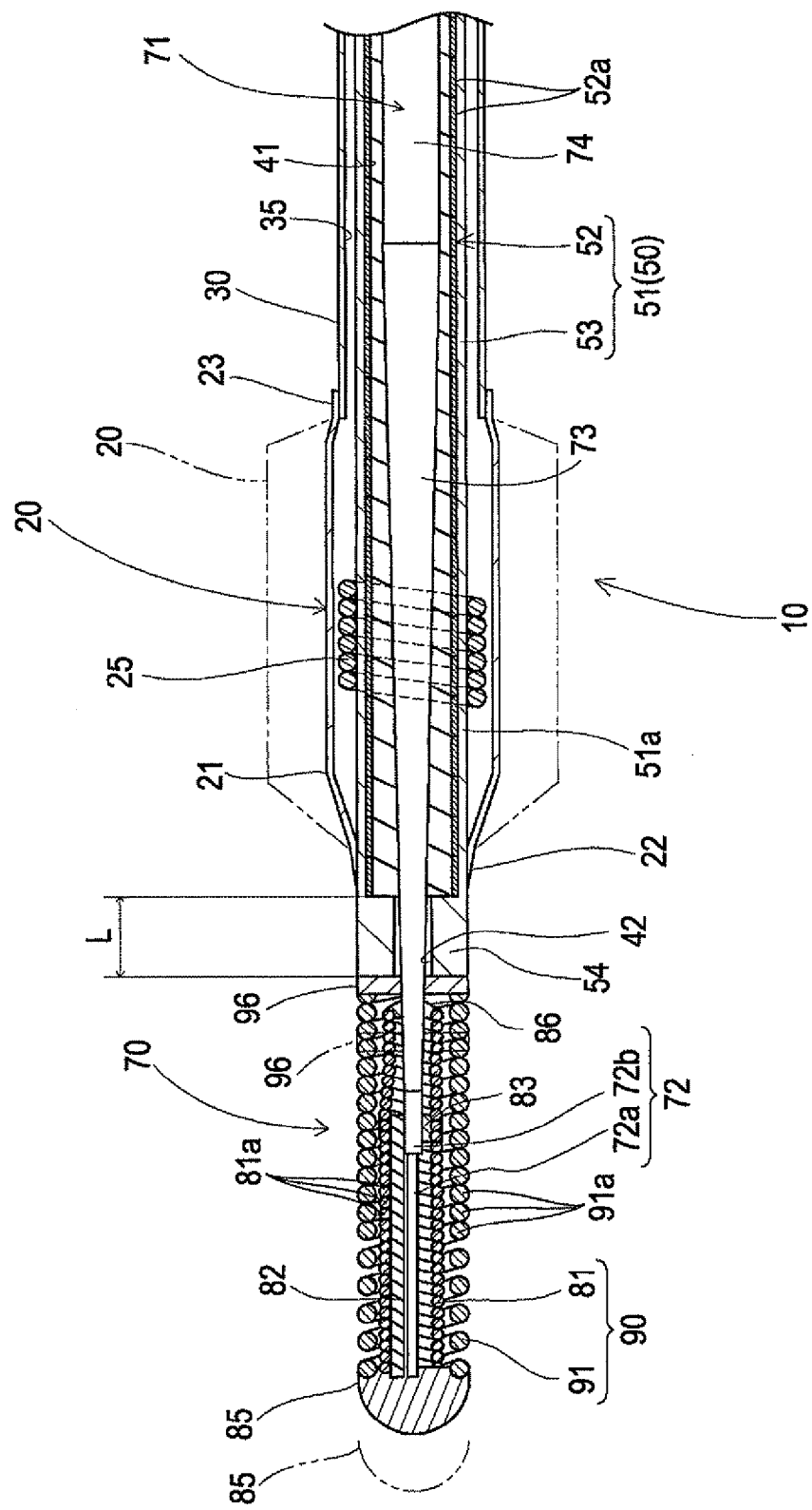
FIG. 2 is an enlarged view illustrating a front end portion of the balloon catheter according to the present embodiment.
Figure 5:
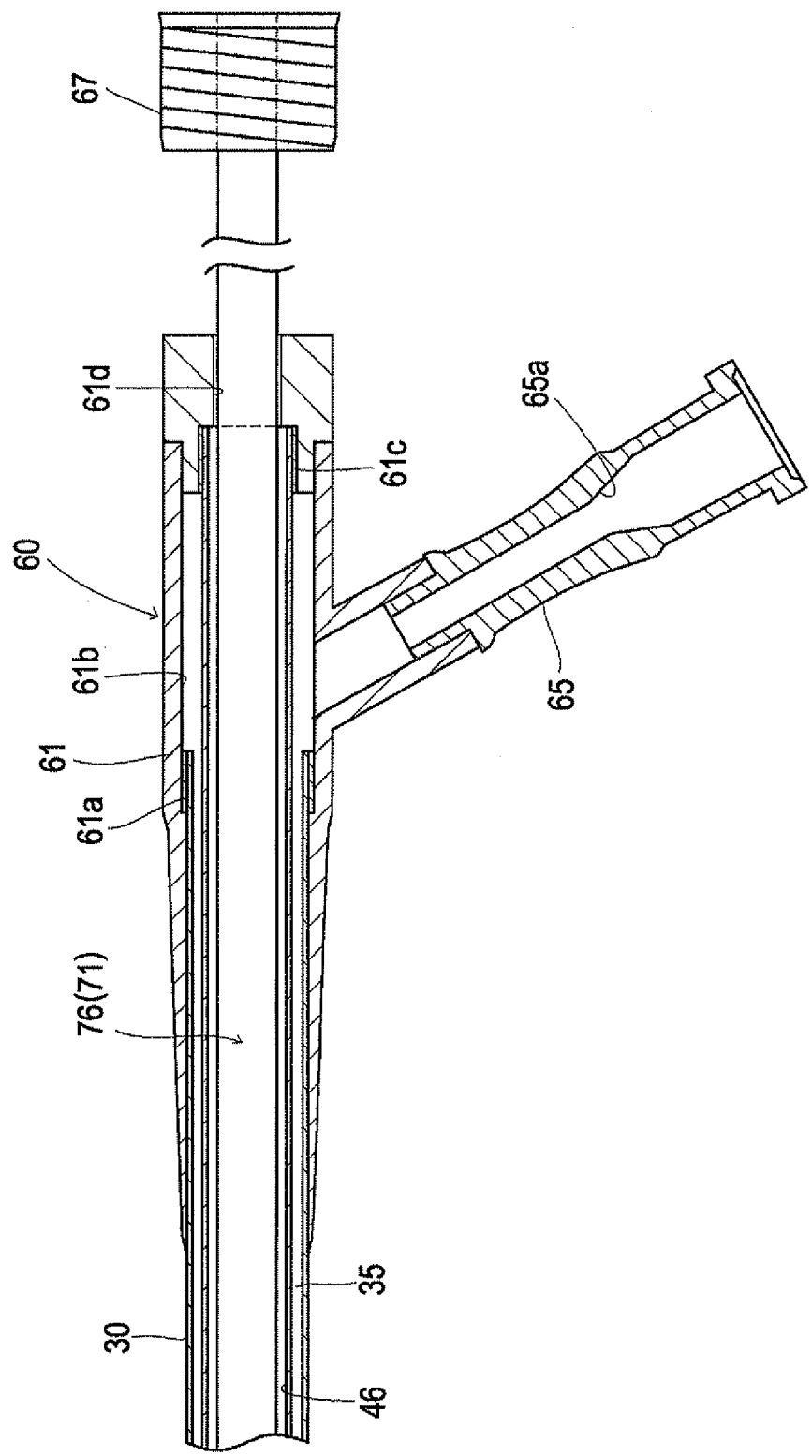
FIG. 5 is a cross-sectional view of a connector according to the present embodiment.

In FIGS. 1, 2 and 5, the left side shown is the front side (distal side) to be inserted into a body, and the right side is the rear side (proximal side, base end side) to be operated by an operator such as a physician.

A balloon catheter 1 is used, for example, to treat an occlusion, a stenosis or the like of a vessel in the heart. The entire length of the balloon catheter 1 is about 1500 mm.

A guidewire 70 is accommodated in a catheter body 10 of the balloon catheter 1. The guidewire 70 is permanently integrated with the catheter body 10. The guidewire 70 is also rotatable about an axis of the catheter body 10 and movable in the axial direction for a predetermined length relative to the catheter body 10.

The catheter body 10 mainly includes a balloon 20, an outer shaft 30, an inner shaft 50 and a connector 60.

The outer shaft 30 is a tube made of resin. A front side of the outer shaft 30 is thinner than a rear side thereof.

The outer shaft 30 has an outer diameter of about 0.50 to about 0.70 mm at the front side thereof. In the present embodiment, the outer diameter of the front side is about 0.60 mm. On the other hand, the outer shaft 30 has an outer diameter of about 0.55 to about 0.75 mm at the rear side thereof. In the present embodiment, the outer diameter of the rear side is about 0.65 mm.

Examples of the material for the resin tube used for the outer shaft 30 include resin such as polyamide, polyamide elastomer, polyolefin, polyester, and polyester elastomer.

The connector 60 is attached to a rear end of the outer shaft 30.

The inner shaft 50 is coaxially arranged inside the outer shaft 30. An inflation lumen 35 for dilating the balloon 20 is formed between the outer shaft 30 and the inner shaft 50. An indeflator (not shown) attached to the connector 60 supplies liquid for dilating the balloon 20. Then, the liquid flows through the inflation lumen 35 to dilate the balloon 20.

The inner shaft 50 includes a front side inner shaft 51 and a rear side inner shaft 56. The front side inner shaft 51 and the rear side inner shaft 56 form a front side guidewire lumen 41 and a rear side guidewire lumen 46, respectively.

Figure 3:
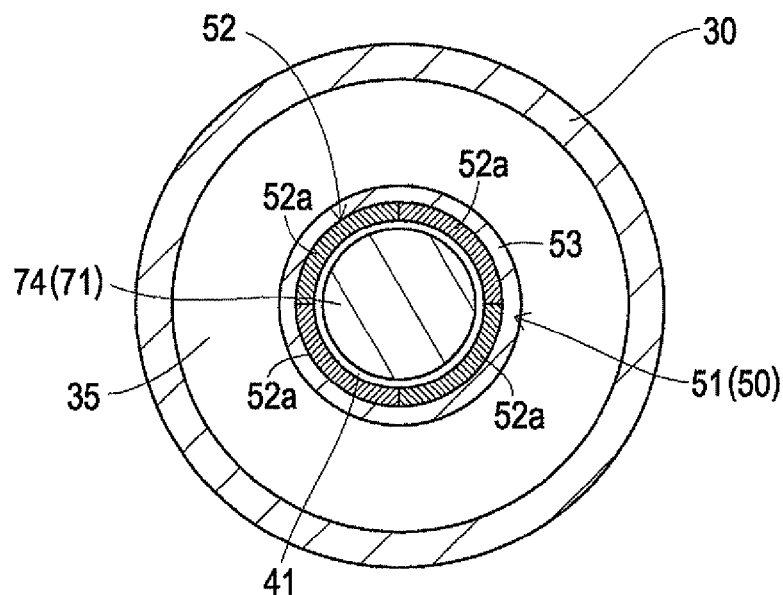
FIG. 3 is a cross-sectional view as seen in the direction of III-III of FIG. 1.
Figure 4:
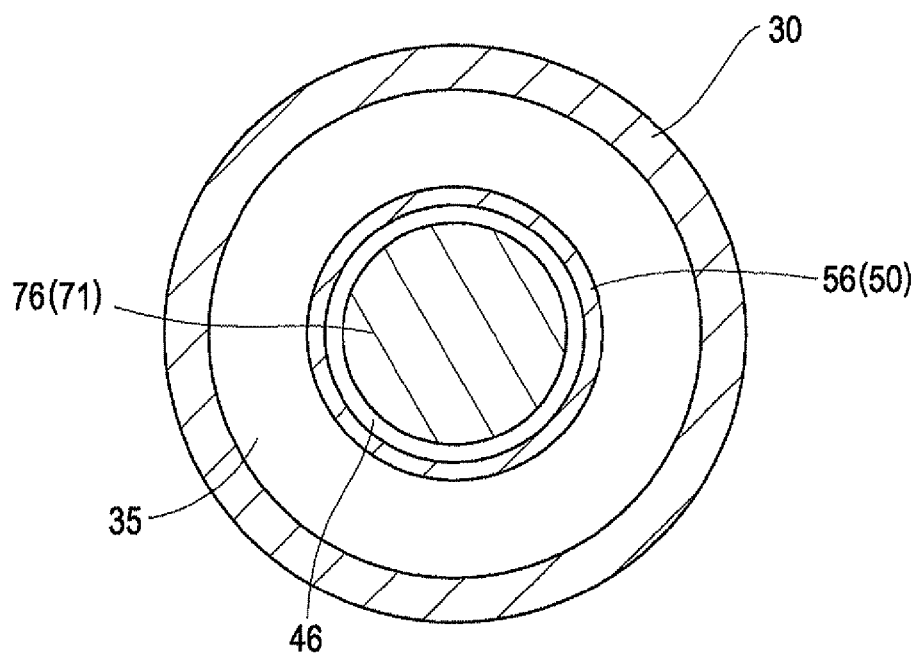
FIG. 4 is a cross-sectional view as seen in the direction of IV-IV of FIG. 1.

As illustrated in FIGS. 2 and 3, the front side inner shaft 51 is a flexible cylindrical member having a stranded wire coil 52 and an outer resin layer 53 coated on an outer circumference of the stranded wire coil 52.

The stranded wire coil 52 is produced by winding a plurality of metal strands 52a spirally around a mandrel so as to be adjacent to each other, eliminating residual stress caused by winding using a known heat treatment, and removing the mandrel.

As illustrated in FIG. 3, four strands 52a are used for the stranded wire coil 52 according to the present embodiment. The strand 52a is a so-called flat wire having a substantially rectangular cross section. The number and size of the strands 52a are appropriately determined in view of the outer and inner diameters and stiffness required for the front side inner shaft 51. The number of the strands 52a is not limited. The strand 52a may alternatively be a round wire having a circular cross section.

The outer resin layer 53 is formed by immersing the stranded wire coil 52 in molten resin contained in a bath and coating the resin on the outer circumference of the stranded wire coil 52. The outer resin layer 53 prevents the liquid for dilating the balloon 20 flowing through the inflation lumen 35 from leaking through gaps between the strands 52a of the stranded wire coil 52 into the front side inner shaft 51.

Such a stranded wire coil 52 enables the inner shaft to have high strength while maintaining flexibility. Thus, the balloon catheter 1 can be prevented from bending. Moreover, the balloon catheter 1 can be made thinner. It is also possible to prevent the front side inner shaft 51 from breaking by pressure by using a balloon 20 having high pressure resistance.

In the present embodiment, the front side inner shaft 51 has an outer diameter of about 0.27 mm and an inner diameter of about 0.19 mm.

Note that a heat-shrinkable resin tube may be used to make the outer resin layer 53, and the resin tube is brought into close contact with the stranded wire coil 52 by thermally shrinking the resin tube.

Examples of the material for the outer resin layer 53 include fluorine resin and polyethylene resin in addition to resin similar to that used for the outer shaft 30 described above.

The front side inner shaft 51 has, at a front side thereof, an extension part 51a extending from a front end of the outer shaft 30. A transition part 54 made of resin is provided at a front end of the extension part 51a.

The material for the transition part 54 may be resin similar to that used for the outer resin layer 53 described above.

The transition part 54 is a cylindrical member that constitutes a front end portion of the front side guidewire lumen 41. The transition part 54 covers a front end portion of the stranded wire coil 52. In addition, the transition part 54 is connected smoothly with the external shape of an outer coil 91 of a front end coil part 90 that will be described below. The transition part 54 has, at a front end thereof, a front side guidewire port 42 (front end opening part) that is an open end of the front side guidewire lumen 41.

The length L of the transition part 54 in the axial direction is preferably about 1.0 to 5.0 mm, and is about 3.0 mm in the present embodiment. The transition part 54 has an outer diameter of about 0.27 mm, which is substantially equal to that of the front side inner shaft 51. The front side guidewire port 42 has an inner diameter smaller than that of the front side inner shaft 51. The inner diameter of the front side guidewire port 42 is as small as possible within a range allowing the movement in the axial direction and the turning of a core shaft 71 inserted therein. The inner diameter of the front side guidewire port 42 is about 0.18 mm in the present embodiment.

Note that the gap between the core shaft 71 and the inner circumferential surface of the front side guidewire port 42 is shown in a somewhat exaggerated manner in FIG. 2.

The transition part 54 can be formed integrally with the outer resin layer 53 by coating the tip portion of the stranded wire coil 52 with resin and then extending only the resin toward the front beyond the stranded wire coil 52 during the formation of the outer resin layer 53 by immersing the stranded wire coil 52 in the resin contained in the bath as described above. As a result of forming the transition part 54 integrally with the outer resin layer 53 in this manner, it is possible to firmly attach the transition part 54 to the stranded wire coil 52. Therefore, the front side inner shaft 51 and the transition part 54 can be curved in an integrated manner.

Note that the transition part 54 may be a separate member from the outer resin layer 53.

The balloon 20 is a member made of resin. The balloon 20 has a dilation part 21 for dilating the balloon 20 at the center in the axial direction thereof. The balloon 20 also has a front end attachment part 22 and a rear end attachment part 23 at the front and rear sides thereof, respectively. The front end attachment part 22 is firmly attached to the tip portion of the extension part 51a of the inner shaft 50 with the transition part 54 protruding out. The rear end attachment part 23 is attached to the front end of the outer shaft 30. In the present embodiment, the rear end attachment part 23 is firmly attached to the outer circumferential surface of the front end of the outer shaft 30.

Note that solid lines in FIGS. 1 and 2 illustrate a state where the balloon 20 is folded before use. Alternate long and two short dashes lines in FIG. 2 illustrate a state where the balloon 20 is dilated.

A marker 25 is attached at the center inside the dilation part 21 of the balloon 20 at the extension part 51a of the front side inner shaft 51. The marker 25 is constituted by a coil formed by winding one strand made of a radiopaque alloy including platinum or the like.

The rear side inner shaft 56 is a tubular member made of metal, a so-called hypotube, having therein the rear side guidewire lumen 46. A tip portion of the rear side inner shaft 56 is inserted into, and firmly attached to, a rear end portion of the front side inner shaft 51. As a result, the rear side guidewire lumen 46 is in communication with the front side guidewire lumen 41.

In the present embodiment, the rear side inner shaft 56 has an outer diameter of about 0.33 mm and an inner diameter of about 0.29 mm. The material for the rear side inner shaft 56 is not particularly limited, and stainless steel is used as the material in the present embodiment. Other materials that may be used include a super elastic alloy such as a Ni—Ti alloy. Alternatively, a resin tube may be used.

A rear end portion of the rear side inner shaft 56 is attached to the connector 60.

Next, the guidewire 70 accommodated in the inner shaft 50 will be described. The guidewire 70 mainly includes the core shaft 71 and the front end coil part 90. The front end coil part 90 includes an inner coil 81 and an outer coil 91.

The core shaft 71 is a member having a circular cross-section and becomes thinner toward a front end thereof so that the core shaft 71 is more flexible toward the front end. The core shaft 71 includes a most distal portion 72, a first tapered portion 73, a first cylindrical portion 74, a second tapered portion 75 and a second cylindrical portion 76 in this order from the front end thereof. The first cylindrical portion 74 and the second cylindrical portion 76 each have a constant diameter. On the other hand, the first tapered portion 73 and the second tapered portion 75 each have an outer diameter gradually decreasing so as to become thinner toward the front end.

The front portion of the core shaft 71 beyond the thinner first cylindrical portion 74 toward the front end is mainly accommodated in the front side inner shaft 51. The second cylindrical portion 76 and the second tapered portion 75 that have the largest diameter are accommodated in the rear side inner shaft 56. Predetermined gaps are formed between an outer circumferential surface of the first cylindrical portion 74 and an inner circumferential surface of the front side inner shaft 51, and between an outer circumferential surface of the second cylindrical portion 76 and an inner circumferential surface of the rear side inner shaft 56, respectively. These gaps allow the guidewire 70 to turn around the axis and move in the axial direction for a predetermined length inside the inner shaft 50. In the present embodiment, the length for which the guidewire 70 can move in the axial direction is set to be about 3.0 to 5.0 cm.

The material for the core shaft 71 is not particularly limited, and stainless steel (SUS304) is used as the material for the core shaft 71 in the present embodiment. Other materials that may be used include a super elastic alloy such as a Ni—Ti alloy, a piano wire and the like.

Note that additional tapered portions or cylindrical portions may be provided as necessary between the tapered portions 73 and 75 and the cylindrical portions 74 and 76. The angle and the size of the tapered portions can also be appropriately set as necessary.

The most distal portion 72 of the core shaft 71 is arranged inside the inner coil 81 that will be described below. The most distal portion 72 of the core shaft 71 includes a first flexible portion 72a at the front side and a second flexible portion 72b at the rear side thereof. The most distal portion 72 is made as thin as possible so that a restorability thereof is enhanced. Specifically, the most distal portion 72 has such characteristic that even if the front end of the guidewire 70 is under a load during an operation, the front end is restored without bending by plastic deformation. In addition, the most distal portion 72 is to be subjected to a process called shaping. Shaping is a process of intentionally bending the front end of the guidewire 70 in a desired direction in advance by an operator such as a physician.

The first flexible portion 72a and the second flexible portion 72b each have a circular cross-section with a constant diameter. The first flexible portion 72a has a smaller diameter than the second flexible portion 72b. Thus, there is a very small tapered portion (not shown) between the first flexible portion 72a and the second flexible portion 72b.

Note that the first flexible portion 72a may be formed by press working into a flat portion having a substantially rectangular cross section.

The inner coil 81 is attached to surround the most distal portion 72 and the tip portion of the first tapered portion 73 of the core shaft 71. The stranded wire coil constituting the inner coil 81 has both stiffness and flexibility. Thus, the most distal portion 72 can be made thinner without deteriorating the flexibility and the stiffness of the front end coil part 90 by surrounding the most distal portion 72 with the inner coil 81. As a result, the restorability of the most distal portion 72 as described above can be enhanced. The inner coil 81 is also stiff in the axial direction. It is thus possible to prevent a decrease in the transmissibility of the pushing force that is a force of the guidewire 70 pushing in the axial direction even if the most distal portion 72 becomes so thin that the stiffness thereof is lowered.

The inner coil 81 is a hollow stranded wire coil produced by winding a plurality of metal strands 81a spirally around a mandrel so as to be adjacent to each other, eliminating residual stress caused by winding using a known heat treatment, and removing the mandrel. The inner coil 81 has an outer diameter of about 0.17 mm in the present embodiment. In addition, the inner coil 81 has a length in the axial direction of about 33.0 mm.

Six strands 81a are used for the inner coil 81. The strands 81a each have a diameter of about 0.03 mm. The number and the diameter of the strands 81a are appropriately determined in view of the outer diameter and the stiffness required for the inner coil 81, and are not limited to these values.

The material for the strand 81a is not particularly limited, and stainless steel is used as the material for the strand 81a in the present embodiment. Other materials that may be used include a super elastic alloy such as a Ni—Ti alloy. Furthermore, the inner coil 81 may be formed of a combination of strands made of different materials.

A front end of the inner coil 81 is bonded to a front end of the core shaft 71 together with a front end of the outer coil 91 by brazing around the axis of the core shaft 71. The brazed portion forms a substantially semispherical coil tip 85 (front end joint). A rear end of the inner coil 81 is bonded to the first tapered portion 73 by brazing. The brazed portion forms an inner rear end joint 86.

A safety wire 82 is attached between the coil tip 85 and the second flexible portion 72b in the inner coil 81 and substantially parallel to the most distal portion 72 of the core shaft 71. The safety wire 82 is to prevent the most distal portion 72 or the like of the guidewire 70 from being separated when the most distal portion 72 or the like is overloaded inside a body.

The safety wire 82 is a stranded wire produced by twisting a plurality of metal strands (seven strands, for example) together. The safety wire 82 has an outer diameter of about 0.042 mm in the present embodiment.

The material for the strand of the safety wire 82 is not particularly limited, and stainless steel is used as the material for the strand in the present embodiment. Furthermore, the safety wire 82 may be formed of a combination of the strands made of different materials.

Note that it is advantageous to use such a stranded wire as the safety wire 82 in terms of producing a safety wire that is flexible and less likely to break. However, the safety wire 82 may alternatively be formed using a single wire or a flat wire rod having a substantially rectangular cross section.

A front end of the safety wire 82 is bonded to the front end of the core shaft 71 at the coil tip 85 together with the inner coil 81 and the outer coil 91 by brazing. A rear end of the safety wire 82 is bonded to the second flexible portion 72b together with the inner coil 81 by brazing, which thereby forms an inner intermediate joint 83. Note that the inner intermediate joint 83 is not bonded to the outer coil 91.

The outer coil 91 surrounds the inner coil 81. The outer coil 91 is formed by winding one strand 91a made of metal. The outer coil 91 has an outer diameter of about 0.30 mm in the present embodiment. The outer diameter of the outer coil 91 is set to be slightly larger than that of the transition part 54.

The strand 91a of the outer coil 91 is formed of a radiopaque metal wire such as a platinum alloy. Alternatively, a single strand formed by bonding a radiopaque metal wire to a radiolucent metal wire such as stainless steel may be used as the strand 91a.

At a front side of the outer coil 91, the strand 91a is open coiled in a manner that gaps are formed between turns of the strand 91a so as to increase flexibility. At a rear side of the outer coil 91, on the other hand, the strand 91a is close coiled in a manner that adjacent turns of the strand 91a are substantially in contact with each other.

The front end of the outer coil 91 is bonded to the front end of the core shaft 71 coaxially with the inner coil 81 at the coil tip 85 by brazing. A rear end of the outer coil 91 is bonded to the first tapered portion 73 by brazing. The brazed portion forms an outer rear end joint 96. The bonding position of the outer rear end joint 96 is located rearward of the inner rear end joint 86 of the inner coil 81.

The outer rear end joint 96 of the outer coil 91 is rotatable relative to the front endface of the transition part 54 in contact therewith. The outer rear end joint 96 is also movable for a predetermined length from the front endface of the transition part 54 as described above, in addition to being relatively rotatable in this manner. The outer diameter of the outer coil 91 herein is set to be slightly larger than that of the transition part 54. Accordingly, when the core shaft 71 of the guidewire 70 is pulled rearward and the outer rear end joint 96 of the outer coil 91 is pressed against the front endface of the transition part 54, the transition part 54 made of resin stretches slightly in the radial direction. As a result, the rear end of the outer coil 91 is smoothly connected with the transition part 54. Therefore, the endface of the transition part 54 is prevented from coming in contact with an inner wall of a vessel, a strut of an indwelling stent or the like and getting stuck therein even if a curve is formed between the outer rear end joint 96 and the transition part 54. Thus, the advancing of the balloon catheter 1 in a vessel is prevented from being blocked and the endface of the transition part 54 is prevented from damaging inside of a body.

A rear end portion of the guidewire 70 is attached to the connector 60.

The connector 60 is a member having a substantially Y-shape, and mainly includes a body part 61, a fluid port part 65 and an operating part 67.

As illustrated in FIG. 5, the body part 61 has therein a front end fixing portion 61a, a fluid chamber 61b, a rear end fixing portion 61c and a rear side guidewire port 61d that are formed coaxially in this order from the front side.

The rear end portions of the outer shaft 30 and the inner shaft 50 are inserted through the front end fixing portion 61a. The front end fixing portion 61a is a portion that liquid-tightly fixes the rear end of the outer shaft 30 to the connector 60.

The fluid chamber 61b is connected to the inflation lumen 35. The fluid chamber 61b is also a portion into which the liquid for dilating the balloon 20 supplied through the fluid port part 65 flows.

The rear end fixing portion 61c is a portion that liquid-tightly fixes the rear end of the inner shaft 50, which extends from the rear end of the outer shaft 30 through the fluid chamber 61b, to the connector 60.

The rear side guidewire port 61d is a portion through which the rear end portion of the guidewire 70 extends from the rear end of the inner shaft 50. The rear end of the guidewire 70 is firmly attached to the operating part 67.

The fluid port part 65 is a portion branching and extending from the body part 61 and has a fluid supply passage 65a. One end of the fluid supply passage 65a communicates with the fluid chamber 61b. The indeflator (not shown) is connected to the other end of the fluid supply passage 65a. With this configuration, the liquid, such as a contrast agent or saline, for dilating the balloon 20 is supplied from the indeflator into the connector 60, and then supplied to the balloon 20 through the inflation lumen 35. The balloon 20 is thus dilated.

The operating part 67 is for operating the guidewire 70. An operator such as a physician can turn the front end coil part 90 of the guidewire 70 and move the front end coil part 90 in the axial direction by turning the operating part 67 around an axis of the body part 61 and moving the operating part 67 in the axial direction relative to the body part 61.

A case of using the balloon catheter 1 according to the present embodiment in an operation of dilating a stenosis in a coronary artery of the heart will be described based on the above configuration.

The balloon catheter 1 is inserted into the coronary artery of the heart where the stenosis as a target to be treated is located. The balloon catheter 1 integrally accommodates the guidewire 70. Thus, the balloon catheter 1 can be inserted into a vessel without inserting a guidewire into the vessel in advance. In the balloon catheter integrated with the guidewire, the gap between the guidewire lumen and the guidewire can be made as small as possible as compared to a common balloon catheter into which a guidewire can be removably inserted. It is thus possible to reduce the outer diameter of the balloon catheter. As a result, the balloon catheter 1 according to the present embodiment can be made to advance into a vessel with relative ease.

In particular, when the balloon catheter according to the present embodiment is used for a technique (the so-called kissing balloon technique) in which a plurality of balloon catheters is used at the same time, the balloon catheters can be inserted easily since the diameter thereof is reduced. Moreover, since the guidewire is accommodated inside the catheter, it is possible to effectively prevent the guidewire and the catheter from getting tangled with each other.

Figure 6:
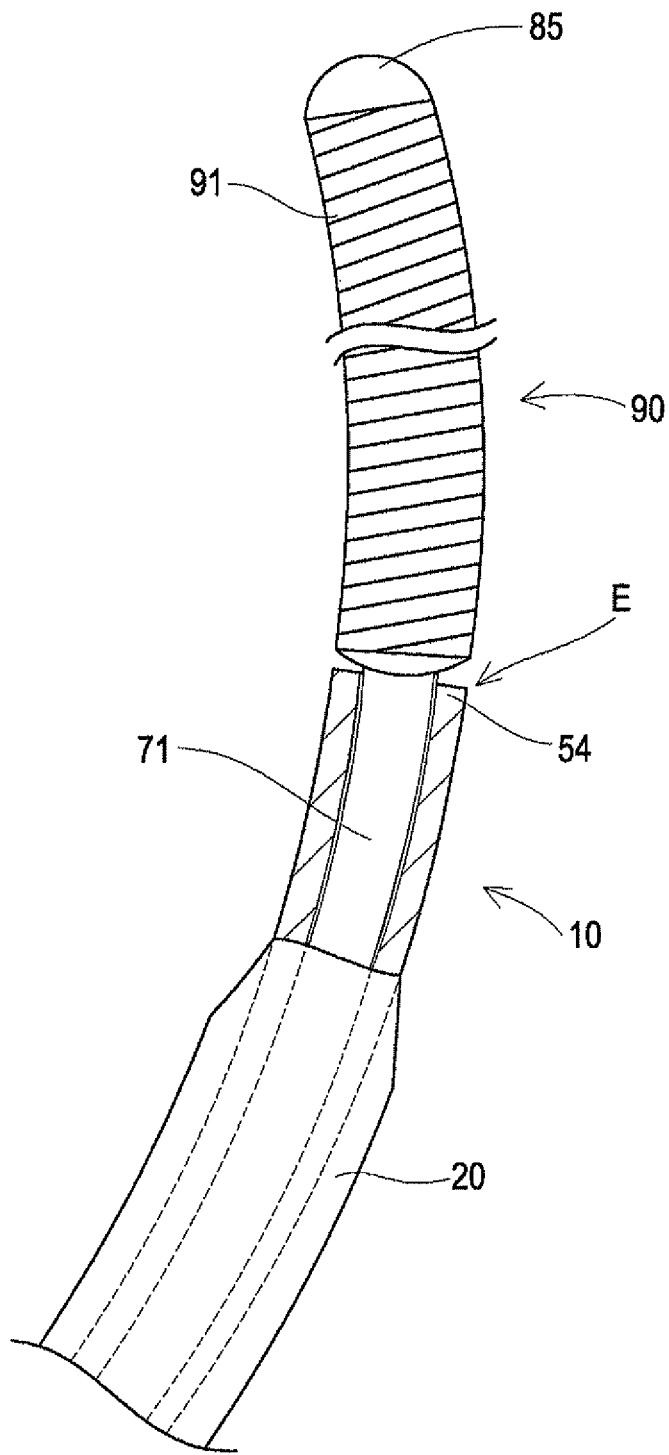
FIG. 6 is an explanatory drawing illustrating a function of the balloon catheter according to the present embodiment.

While the balloon catheter 1 is advanced into a vessel, the catheter body 10 and the guidewire 70 advance integrally. At this time, it is preferable to pull the operating part 67 toward the proximal side so as to position the guidewire 70 rearward when the balloon catheter 1 passes through a curved vessel or the like. As a result, the front end coil part 90 of the guidewire 70 and the catheter body 10 are connected by the transition part 54 as illustrated in FIG. 6. It is thus possible to prevent, as much as possible, a stepped portion from being formed between the outer coil 91 of the guidewire 70 and the transition part 54. Therefore, the balloon catheter 1 is curved smoothly. Specifically, the transition part 54 has a flexible structure made of resin. The transition part 54 is thus curved flexibly under an external force applied to the boundary between the front end coil part 90 of the guidewire 70 and the front end portion of the catheter body 10. As a result, the portion between the outer coil 91 and the catheter body 10 is curved smoothly.

In addition, the outer diameter of the outer coil 91 is set to be slightly larger than that of the transition part 54. As a result, it is possible to prevent, as much as possible, a corner E of the front endface of the transition part 54 from getting stuck in an inner wall of a vessel, a strut of an indwelling stent or the like. Note that the neighboring part of the corner E is shown in an exaggerated manner in FIG. 6 for easier understanding.

When the front end coil part 90 is pulled toward the proximal side, the outer rear end joint 96 at the rear end of the outer coil 91 comes in contact with the catheter body 10 on the side of the front side inner shaft 51 having the stranded wire coil 52. However, the transition part 54 made of resin is present therebetween. Thus, the front end coil part 90 made of metal and the stranded wire coil 52 also made of metal in the front side inner shaft 51 do not directly and strongly come into contact with each other even when the front end coil part 90 is pulled toward the proximal side. It is therefore possible to prevent, as much as possible, the movable portion between the front end coil part 90 and the catheter body 10 from being damaged.

There is a possibility that the front end coil part 90 and the catheter body 10 strongly come into contact with each other with the transition part 54 interposed therebetween as described above. However, the resin forming the transition part 54 is formed integrally with the outer resin layer 53 that covers the stranded wire coil 52 in the front side inner shaft 51. As a result, the transition part 54 is prevented, as much as possible, from falling off. The balloon catheter 1 thus has a highly safe configuration.

If an operator such as a physician intends to turn the front end coil part 90 of the guidewire 70 or move the front end coil part 90 forward or rearward while advancing the balloon catheter 1, the operator operates the operating part 67 of the connector 60. If the operator turns the operating part 67 at the proximal side, the front end coil part 90, namely the outer coil 91 and the inner coil 81, is rotated at the same time through the core shaft 71.

Such turning or forward or rearward movement of the front end coil part 90 is made in a case where the tip portion of the guidewire 70 comes into contact with a tortuous vessel wall and the advance of the balloon catheter 1 is thus blocked, or in like cases. Such turning or forward or rearward movement is also performed, in a case where the most distal portion 72 of the core shaft 71 is provided with a shaping and directed, so as to turn the shaped direction to an appropriate direction.

The operator positions the balloon 20 at the stenosis as a target site, using the marker 25 under radioscopy. Subsequently, the liquid for dilation, such as a contrast agent or saline is supplied by the indeflator (not shown) connected to the fluid port part 65 of the connector 60.

At this time, the liquid for dilation flows into the inflation lumen 35 formed between the outer shaft 30 and the inner shaft 50 through the fluid chamber 61b of the body part 61 of the connector 60, and dilates the balloon 20.

Upon completion of the operation of dilating the stenosis with the balloon 20, the operator uses the indeflator to discharge the liquid for dilation out of the balloon 20. That is, the liquid for dilation is discharged from inside the balloon 20 to the indeflator through the inflation lumen 35.

The operation ends in this manner and the balloon catheter 1 is removed from the body.

As described above, the balloon catheter 1 according to the present embodiment has a structure integrally including the guidewire 70. Moreover, in the balloon catheter 1, the external shape of the front end coil part 90 and the external shape of the catheter body 10 are smoothly connected with the transition part 54 interposed therebetween. Accordingly, a stepped portion is substantially not formed between the rear end portion of the front end coil part 90 of the guidewire 70 and the front end portion of the catheter body 10. The balloon catheter 1 is thus flexibly and smoothly curved as a whole. Therefore, it is possible to prevent, as much as possible, the endface of the transition part 54, which is a front end portion of the catheter body 10, from getting stuck in an inner wall of a vessel, a strut of an indwelling stent or the like, and to prevent, as much as possible, reduction in crossability of the balloon catheter 1 caused thereby or for like reasons.

In addition, the transition part 54 is formed integrally with, and using the same resin as, the outer resin layer 53 that covers the stranded wire coil 52 in the front side inner shaft 51. As a result, it is possible to prevent, as much as possible, the transition part 54 from falling off from the balloon catheter 1 when the transition part 54 is curved flexibly.

The inner coil 81 and the safety wire 82 according to the present embodiment described above have advantages that it is possible to improve the restorability of the core shaft 71 and that it is possible to prevent the front end portion of the core shaft 71 from bending, as described above. However, the inner coil 80 and the safety wire 82 are not absolutely necessary elements.

In the embodiments described above, the front end coil part 90 has an outer diameter substantially equal to that of the tip portion of the front side inner shaft 51 of the catheter body 10. Thus, the transition part 54 connecting these elements has a cylindrical shape with a constant outer diameter. If, however, the outer diameter of one of these elements is larger than that of the other, the transition part 54 preferably has a tapered shape or the like having an outer diameter that gradually changes, in order to smoothly connect the two elements having different outer diameters.

Figure 7:
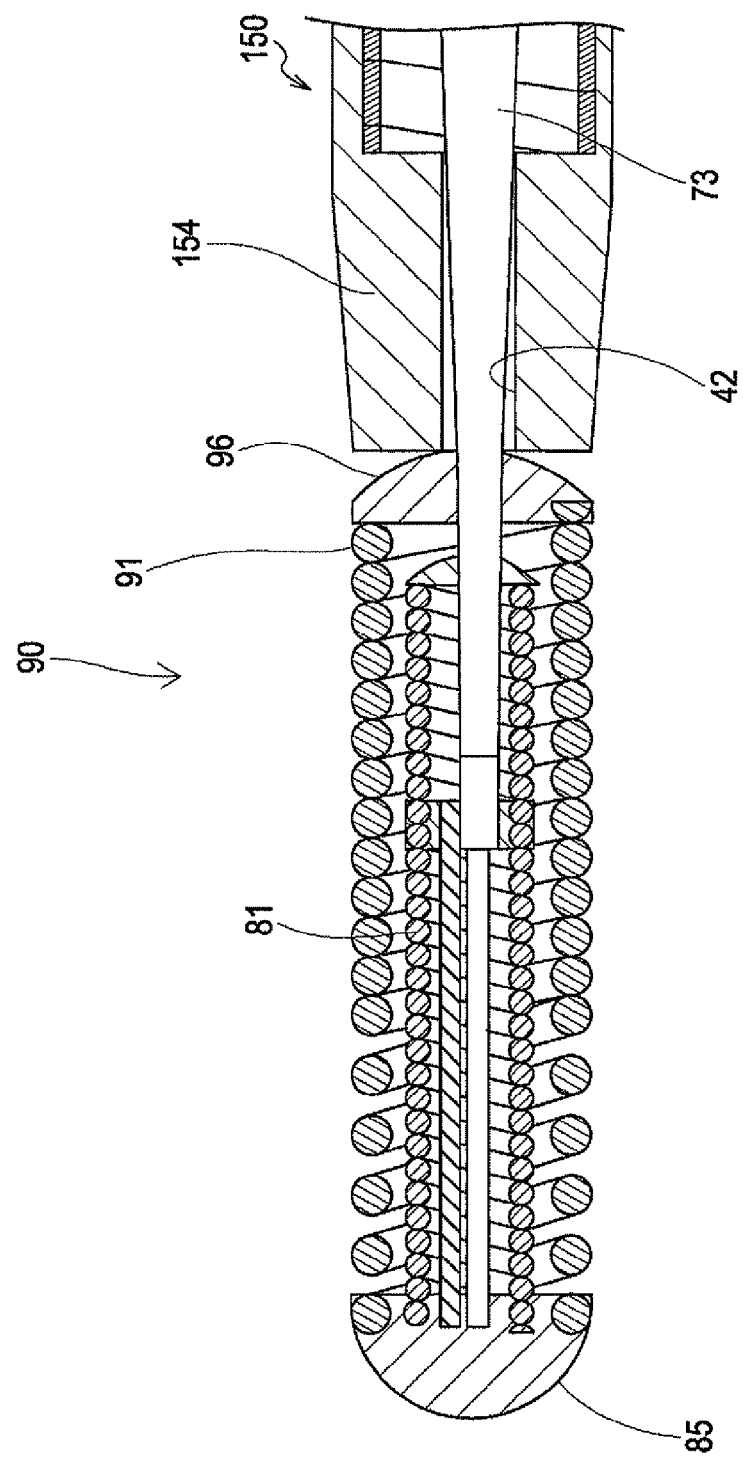
FIG. 7 is a view illustrating a second embodiment.

For example, in a case where the outer diameter of a tip portion of an inner shaft 150 is larger than that of the front end coil part 90, a transition part 154 has a tapered shape with an outer diameter gradually decreasing toward a front end thereof as illustrated in FIG. 7.

In the embodiments described above, the transition part 54 is provided at the catheter body 10. Alternatively, the transition part 54 may be provided at the front end coil part 90. Still alternatively, the transition part 54 may be provided both at the catheter body 10 and at the front end coil part 90.

In the embodiments described above, the guidewire 70 can both turn around the axis of the catheter body 10 and move forward and rearward in the axial direction relative to the catheter body 10. However, the guidewire 70 may be only capable of the turning movement. In such case, the guidewire 70 is preferably configured to relatively turn in a state where the outer rear end joint 96 at the rear end of the outer coil 91 is in contact with the front endface of the transition part 54 so as to narrow, as much as possible, the gap at the boundary between the front end coil part 90 and the catheter body 10.

In the embodiments described above, the stranded wire coil 52 of the front side inner shaft 51 is a stranded wire coil made of a plurality of strands. Alternatively, a single wire coil formed of one strand may be used therefor. However, a stranded wire coil allows maintenance of flexibility and increase in stiffness. Thus, the stranded wire coil 52 is preferably formed of a stranded wire coil made of a plurality of strands as in the embodiments described above. As a result, it is possible to enhance the flexibility of the front side inner shaft 51 and to prevent the front side inner shaft 51 from bending.

The inside of the stranded wire coil 52 may be coated with polyamide resin, fluorine resin, polyethylene resin or the like. More preferably, low-friction resin is used for the coating.

Furthermore, in the embodiments described above, the inner shaft 50 is constituted by two shafts of the front side inner shaft 51 and the rear side inner shaft 56. Alternatively, the inner shaft 50 may be constituted by one shaft having a stranded wire coil similar to that of the front side inner shaft 51.

In the catheter body 10 according to the embodiments described above, the inner shaft 50 forming the guidewire lumen and the outer shaft 30 forming the inflation lumen are separate members. In addition, the inner shaft 50 extends toward the front side farther than the outer shaft 30.

Alternatively, one shaft having a plurality of lumens including the guidewire lumen and the inflation lumen may be arranged in the catheter body.

In this case, the transition part is preferably formed to smoothly connect the external shape of the tip portion of the shaft constituting the catheter body and the external shape of the front end coil part. In this case, the catheter body generally has a larger diameter. As a result, the transition part has a tapered shape with an outer diameter gradually decreasing toward a front end thereof similarly to the example illustrated in FIG. 7.

In the embodiments described above, the balloon catheter 1 is used for treatment of a vessel in the heart. However, the balloon catheter 1 may alternatively be used for various operations including an operation of dilating a vessel in the lower limb or a dialysis shunt.

While the invention has been shown and described in detail, the foregoing description is in all aspects illustrative and not restrictive. It is therefore understood that numerous modifications and variations can be devised without departing from the spirit and scope of the invention.

The invention claimed is:

1. A balloon catheter integrally accommodating a guidewire, comprising:
    a catheter body that includes a balloon, an inflation lumen for supplying a fluid for dilating the balloon and a guidewire lumen for accommodating the guidewire;
    a core shaft inserted in the guidewire lumen;
    a front end coil part formed of at least one wound strand and surrounding a front end portion of the core shaft extending from a front end of the catheter body;
    a transition part made of resin that is provided between a rear end of the front end coil part and a front end of the catheter body and smoothly connects an external shape of the front end coil part and an external shape of a front end portion of the catheter body; and
    a joint bonded to the rear end of the front end coil part and the front end portion of the core shaft, wherein
        the transition part is in contact with the joint, and
        the joint is rotatable relative to the transition part.

2. The balloon catheter according to claim 1, wherein
the catheter body includes a tubular outer shaft and an inner shaft that is inserted in the outer shaft and forms the guidewire lumen,
the inner shaft extends from a front end of the outer shaft, and
the transition part smoothly connects the external shape of the front end coil part and the external shape of the tip portion of the inner shaft.

3. The balloon catheter according to claim 1, wherein
the catheter body includes an inner shaft that forms the guidewire lumen,
the inner shaft includes a second coil that is different from the front end coil part and that is formed by winding at least one strand and a resin layer made of resin, a front end of the inner shaft being formed of resin that forms the transition part.

4. The balloon catheter according to claim 1, wherein
an outer diameter of the front end coil part is larger than that of the transition part.

5. The balloon catheter according to claim 1, wherein
the transition part has a tapered shape with an outer diameter decreasing from the front end of the catheter body toward the rear end of the front end coil part.

* * * * *